(12) United States Patent
Ito et al.

(10) Patent No.: US 9,909,980 B2
(45) Date of Patent: Mar. 6, 2018

(54) FLUID ANALYZER AND METHOD OF MANUFACTURING FLUID ANALYZER

(71) Applicant: HAMAMATSU PHOTONICS K.K., Hamamatsu-shi, Shizuoka (JP)

(72) Inventors: Akio Ito, Hamamatsu (JP); Tatsuo Dougakiuchi, Hamamatsu (JP); Tadataka Edamura, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/294,882

(22) Filed: Oct. 17, 2016

(65) Prior Publication Data

US 2017/0115213 A1 Apr. 27, 2017

(30) Foreign Application Priority Data

Oct. 21, 2015 (JP) ................................ 2015-207249
Jul. 5, 2016 (JP) ................................ 2016-133408

(51) Int. Cl.
*G01N 21/00* (2006.01)
*G01N 21/39* (2006.01)
(Continued)

(52) U.S. Cl.
CPC ........... *G01N 21/39* (2013.01); *H01S 5/0264* (2013.01); *H01S 5/3401* (2013.01);
(Continued)

(58) Field of Classification Search
CPC ... H01S 5/12; H01S 5/34; H01S 5/022; H01S 5/0264; H01S 5/3401; H01S 5/02228;
(Continued)

(56) References Cited

U.S. PATENT DOCUMENTS 4,849,637 A 7/1989 Cerff et al.
2010/0029026 A1* 2/2010 Berger .................. B82Y 20/00
438/24

FOREIGN PATENT DOCUMENTS

JP S63-165735 A 7/1988

OTHER PUBLICATIONS

Benedikt Shwarz et al., "Monolithically integrated mid-infrared lab-on-a-chip using plasmonics and quantum cascade structures," Nature Communications, Jun. 6, 2014, pp. 1-7.

* cited by examiner

*Primary Examiner* — Jamil Ahmed
(74) *Attorney, Agent, or Firm* — Drinker Biddle & Reath LLP

(57) ABSTRACT

A fluid analyzer includes a substrate, a quantum cascade laser formed on a surface of the substrate and including a first light-emitting surface and a second light-emitting surface facing each other, a first quantum cascade detector formed on the surface and including the same layer structure as the quantum cascade laser and a first light incident surface facing the first light-emitting surface, a second quantum cascade detector formed on the surface and including the same layer structure as the quantum cascade laser and a second light incident surface facing the second light-emitting surface, and a resin member covering at least the second light-emitting surface and the second light incident surface and having optical transparency and an electrical insulation property. A first space in which a fluid to be analyzed is disposed is provided in a first area between the first light-emitting surface and the first light incident surface.

9 Claims, 12 Drawing Sheets

(51) Int. Cl.
  *H01S 5/34* (2006.01)
  *H01S 5/026* (2006.01)
  *H01S 5/22* (2006.01)
(52) U.S. Cl.
  CPC .......... *G01N 2021/399* (2013.01); *H01S 5/22* (2013.01); *H01S 2301/176* (2013.01)
(58) Field of Classification Search
  CPC ... H01S 2301/176; H01S 21/00; G01N 21/39; G01N 2021/399
  See application file for complete search history.

FLUID ANALYZER AND METHOD OF MANUFACTURING FLUID ANALYZER

TECHNICAL FIELD

The present disclosure relates to a fluid analyzer and a method of manufacturing the fluid analyzer.

BACKGROUND

In a device disclosed in Japanese Unexamined Patent Publication No. S63-165735, a beam emitted from one end face of a laser is detected through a gas, which is present in a measuring tank, by a wave detector, and a beam emitted from the other end face of the laser is detected through a reference gas, which is present in a reference tank, by another wave detector. According to this device, since signals output from the two wave detectors are simultaneously acquired, differential optical absorption spectroscopy measurement is performed for the gas present in the measuring tank and the gas can be analyzed.

SUMMARY

However, since the laser, the measuring tank, the reference tank, and the two wave detectors are separately provided in the device disclosed in Japanese Unexamined Patent Publication No. 563465735, it is difficult to simplify the structure of the device while maintaining the accuracy of analysis for a gas.

Accordingly, an object of an aspect of the disclosure is to provide a fluid analyzer that can accurately analyze a fluid by a simple structure and a method of manufacturing the fluid analyzer.

A fluid analyzer according to an aspect of the disclosure includes a substrate, a quantum cascade laser formed on a surface of the substrate and including a first light-emitting surface and a second light-emitting surface facing each other in a predetermined direction parallel to the surface, a first quantum cascade detector formed on the surface and including the same layer structure as the quantum cascade laser and a first light incident surface facing the first light-emitting surface in the predetermined direction, a second quantum cascade detector formed on the surface and including the same layer structure as the quantum cascade laser and a second light incident surface facing the second light-emitting surface in the predetermined direction, and a resin member covering at least the second light-emitting surface and the second light incident surface and having optical transparency for an oscillation wavelength of the quantum cascade laser and an electrical insulation property. A first space in which a fluid to be analyzed is disposed is provided in a first area between the first light-emitting surface and the first light incident surface.

Since signals output from the first quantum cascade detector and the second quantum cascade detector are simultaneously acquired, the fluid analyzer can perform differential optical absorption spectroscopy measurement for the fluid to be analyzed and can analyze the fluid. Here, the quantum cascade laser, the first quantum cascade detector, and the second quantum cascade detector include the same layer structure. Accordingly, since the quantum cascade laser, the first quantum cascade detector, and the second quantum cascade detector have the same quantum cascade structure, the oscillation wavelength of the quantum cascade laser reliably overlaps the detection wavelength of each of the first quantum cascade detector and the second quantum cascade detector. Further, the quantum cascade laser, the first quantum cascade detector, and the second quantum cascade detector are formed on the surface of the same substrate. Accordingly, since the temperatures of the quantum cascade laser, the first quantum cascade detector, and the second quantum cascade detector are uniformized through the substrate, it is difficult for the change in the ambient temperature to affect the result of the differential optical absorption spectroscopy measurement. Therefore, according to the fluid analyzer, a fluid can be accurately analyzed by a simple structure.

In the fluid analyzer according to the aspect of the disclosure, the resin member may be disposed on all of a second area between the second light-emitting surface and the second light incident surface, and may allow the first light-emitting surface, the first light incident surface, and all of the first area to be exposed to the outside. Accordingly, differential optical absorption spectroscopy measurement can be performed for the fluid (for example, gas) disposed in the first space while the resin member itself is used as a reference material.

In the fluid analyzer according to the aspect of the disclosure, the resin member may be disposed on all of a second area between the second light-emitting surface and the second light incident surface, and may include a first recess defining the first space in the first area and may cover the first light-emitting surface and the first light incident surface. Accordingly, differential optical absorption spectroscopy measurement can be performed for the fluid (for example, gas or liquid) disposed in the first space while the resin member itself is used as a reference material. Particularly, the first space is defined by the first recess of the resin member. Accordingly, when the fluid to be analyzed is liquid, the liquid can be stably disposed in the first space.

In the fluid analyzer according to the aspect of the disclosure, the first recess may be opened to a side opposite to the substrate. Accordingly, when the fluid to be analyzed is liquid, the liquid can be more stably disposed in the first space.

In the fluid analyzer according to the aspect of the disclosure, the resin member may include a second recess defining a second space in a second area between the second light-emitting surface and the second light incident surface and may cover the second light-emitting surface and the second light incident surface, and may include a first recess defining the first space in the first area and may cover the first light-emitting surface and the first light incident surface. Accordingly; while a predetermined material is disposed in the second space and the material is used as a reference material, differential optical absorption spectroscopy measurement can be performed for the fluid (for example, gas or liquid) disposed in the first space. Particularly, the first space is defined by the first recess of the resin member. Accordingly, when the fluid to be analyzed is liquid, the liquid can be stably disposed in the first space. Likewise, the second space is defined by the second recess of the resin member. Accordingly, when the predetermined material serving as the reference material is liquid, the liquid can be stably disposed in the second space.

In the fluid analyzer according to the aspect of the disclosure, each of the first recess and the second recess may be opened to a side opposite to the substrate. Accordingly, when the fluid to be analyzed is liquid, the liquid can be more stably disposed in the first space. Likewise, when the predetermined material serving as the reference material is liquid, the liquid can be more stably disposed in the second space.

In the fluid analyzer according to the aspect of the disclosure, the width of each of the first quantum cascade detector and the second quantum cascade detector in a direction parallel to the surface and perpendicular to the predetermined direction may be larger than the width of the quantum cascade laser in the direction parallel to the surface and perpendicular to the predetermined direction. Accordingly, the laser beam, which is emitted from the first light-emitting surface of the quantum cascade laser, can be made to be efficiently incident on the first light incident surface of the first quantum cascade detector. Likewise, the laser beam, which is emitted from the second light-emitting surface of the quantum cascade laser, can be made to be efficiently incident on the second light incident surface of the second quantum cascade detector.

In the fluid analyzer according to the aspect of the disclosure, the quantum cascade laser may be formed as a distributed feedback element, the first light incident surface may be inclined so as to have a positional relationship where an acute angle is formed between the first light incident surface and the first light-emitting surface, and the second light incident surface may be inclined so as to have a positional relationship where an acute angle is formed between the second light incident surface and the second light-emitting surface. Accordingly, since light, which is reflected by the first light incident surface of the first quantum cascade detector, of a laser beam, which is emitted from the first light-emitting surface of the quantum cascade laser becomes return light, it is suppressed that the light is incident on the first light-emitting surface. Since light, which is reflected by the second light incident surface of the second quantum cascade detector, of the laser beam, which is emitted from the second light-emitting surface of the quantum cascade laser, becomes return light, it is suppressed that the light is incident on the second light-emitting surface. Accordingly, since it is suppressed that an oscillation mode is disturbed due to an influence of the return light, stable single-mode oscillation can be obtained in the quantum cascade laser formed as a distributed feedback element and more accurate spectroscopic measurement can be performed.

A method of manufacturing a fluid analyzer according to another aspect of the disclosure includes: a first step of forming a laminated body on a surface of a substrate, the laminated body including a quantum cascade structure; a second step of performing etching on the laminated body, and forming a quantum cascade laser including a first light-emitting surface and a second light-emitting surface facing each other in a predetermined direction parallel to the surface, a first quantum cascade detector including a first light incident surface facing the first light-emitting surface in the predetermined direction, and a second quantum cascade detector including a second light incident surface facing the second light-emitting surface in the predetermined direction; a third step of forming a resin layer on the surface, the resin layer having optical transparency for an oscillation wavelength of the quantum cascade laser and an electrical insulation property, so that the resin layer covers the quantum cascade laser, the first quantum cascade detector, and the second quantum cascade detector; and a fourth step of performing etching on the resin layer, and forming a resin member covering at least the second light-emitting surface and the second light incident surface and forming a first space, in which a fluid to be analyzed is disposed, in a first area between the first light-emitting surface and the first light incident surface.

According to the method of manufacturing the fluid analyzer, the above-mentioned fluid analyzer can be easily and reliably manufactured. Particularly, the quantum cascade laser, the first quantum cascade detector, and second quantum cascade detector having the same quantum cascade structure can be formed on the surface of the substrate with a high positional accuracy.

According to the aspects of the disclosure, it is possible to provide a fluid analyzer that can accurately analyze a fluid by a simple structure and a method of manufacturing the fluid analyzer.

DETAILED DESCRIPTION

Figure 1:
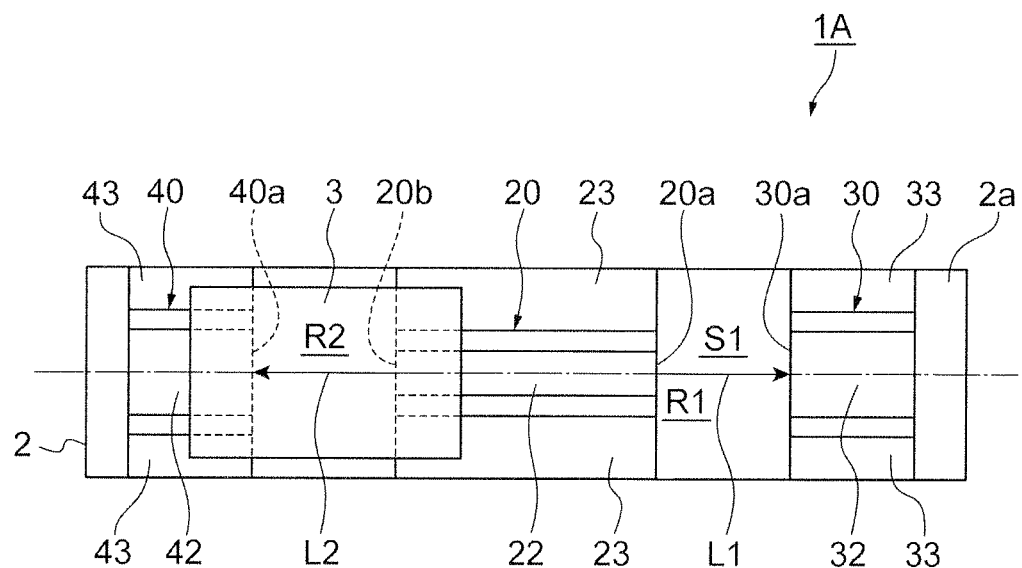
FIG. 1 is a plan view of a fluid analyzer according to a first embodiment of the disclosure.
Figure 1:
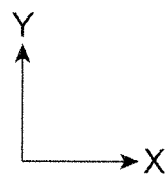

Embodiments of the disclosure will be described in detail below with reference to the drawings. Meanwhile, the same portions or corresponding portions will be denoted by the same reference numerals in the respective drawings and the repeated description thereof will be omitted.

First Embodiment

Figure 2:
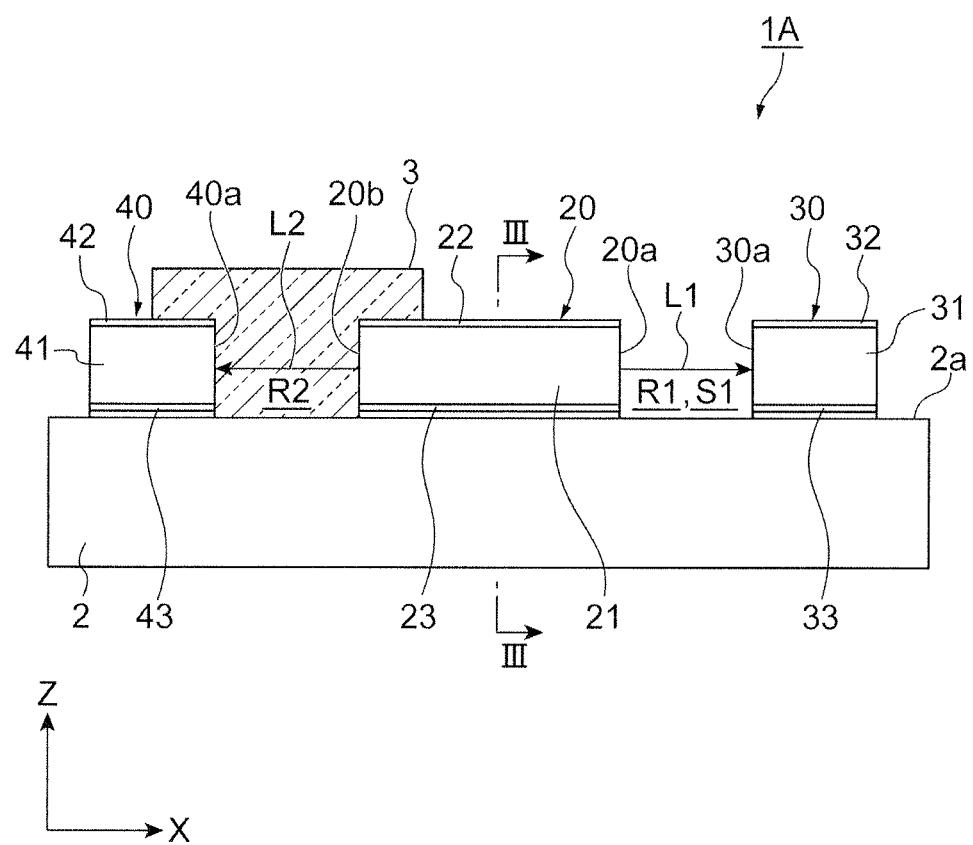
FIG. 2 is a side view of the fluid analyzer of FIG. 1.

As illustrated in FIGS. 1 and 2, a fluid analyzer 1A includes a substrate 2, a quantum cascade laser 20 (hereinafter, referred to as a "QCL 20"), a first quantum cascade detector 30 (hereinafter, referred to as a "first QCD 30"), a second quantum cascade detector 40 (hereinafter, referred to as a "second QCD 40"), and a resin member 3. The substrate 2 is made of, for example, a semi-insulating semiconductor material, such as InP. When being viewed in a Z-axis direction perpendicular to a surface 2a of the substrate 2, the width of the substrate 2 in a Y-axis direction perpendicular to the Z-axis direction is, for example, about several hundred μm and the length of the substrate 2 in an X-axis direction (a predetermined direction parallel to the surface 2a of the substrate 2) perpendicular to the Z-axis direction and Y-axis direction is, for example, about several mm. Meanwhile, only the resin member 3 is illustrated in FIG. 2 as a section taken along a dashed-dotted line of FIG. 1.

The QCL 20 is formed on the surface 2a of the substrate 2. The QCL 20 includes a first light-emitting surface 20a and a second light-emitting surface 20b that face each other in the X-axis direction. The first light-emitting surface 20a and the second light-emitting surface 20b are parallel to a Y-Z plane perpendicular to the X-axis direction. The width of the QCL 20 in the Y-axis direction is in the range of, for example, about several μm to several tens μm, and the length of the QCL 20 in the X-axis direction (resonator length) is, for example, about several mm.

Figure 3:
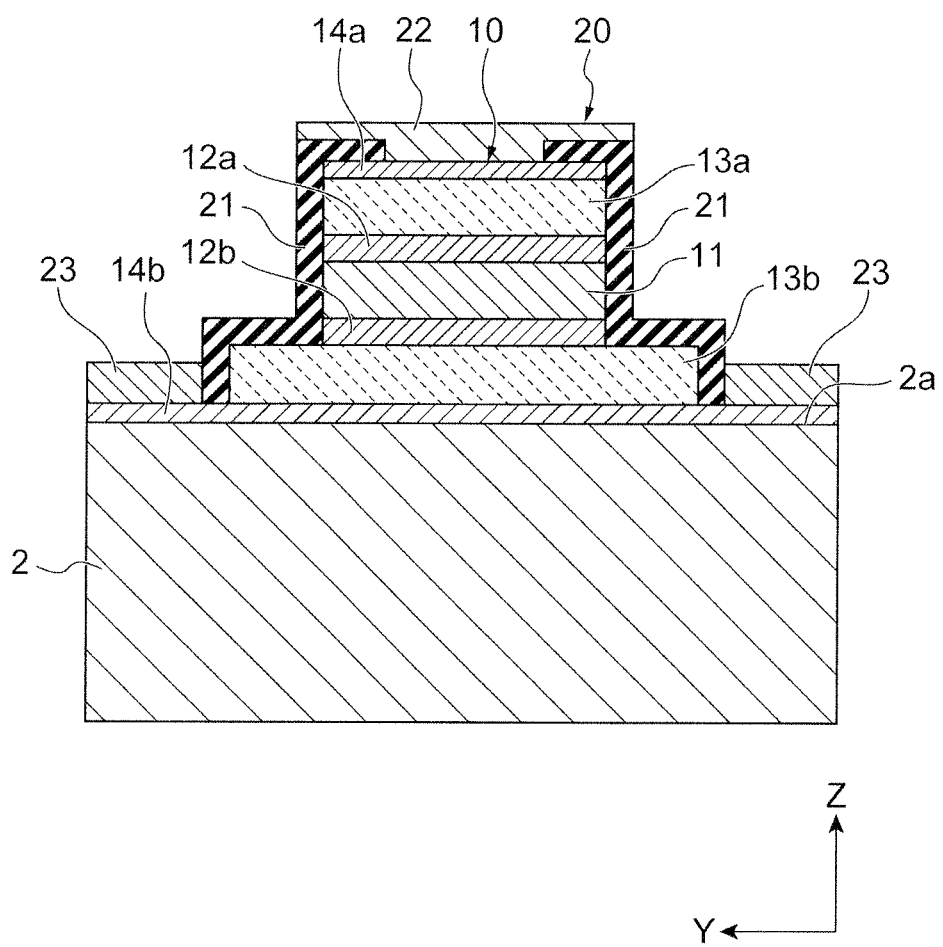
FIG. 3 is a cross-sectional view taken along line of FIG. 2.

As illustrated in FIG. 3, the QCL 20 includes a layer structure 10. The layer structure 10 is a ridge stripe structure that includes an active layer 11, an upper guide layer 12a and a lower guide layer 12b, an upper clad layer 13a and a lower clad layer 13b, and an upper contact layer 14a and a lower contact layer 14b. The lower contact layer 14b is made of, for example, InGaAs and is formed on the surface 2a of the substrate 2. The lower clad layer 13b is made of, for example, InP and is formed on the lower contact layer 14b. The lower guide layer 12b is made of, for example, InGaAs and is formed on the lower clad layer 13b. The active layer 11 has a quantum cascade structure and is formed on the lower guide layer 12b. The upper guide layer 12a is made of, for example, InGaAs and is formed on the active layer 11. The upper clad layer 13a is made of, for example, InP and is formed on the upper guide layer 12a. The upper contact layer 14a is made of, for example, InGaAs and is formed on the upper clad layer 13a.

An example of a quantum cascade structure per cycle of the active layer 11 is shown in Table 1.

TABLE 1

| | Material | Thickness | |
|---|---|---|---|
| Barrier layer 1 | InAlAs | 3.3 nm | undoped |
| Quantum well 1 | InGaAs | 1.9 nm | undoped |
| Barrier layer 2 | InAlAs | 1.2 nm | undoped |
| Quantum well 2 | InGaAs | 6.3 nm | undoped |
| Barrier layer 3 | InAlAs | 1.5 nm | undoped |
| Quantum well 3 | InGaAs | 5.1 nm | undoped |
| Barrier layer 4 | InAlAs | 1.5 nm | undoped |
| Quantum well 4 | InGaAs | 4.5 nm | undoped |
| Barrier layer 5 | InAlAs | 1.8 nm | undoped |
| Quantum well 5 | InGaAs | 3.9 nm | undoped |
| Barrier layer 6 | InAlAs | 1.9 nm | Si: $2 \times 10^{17}/cm^3$ |
| Quantum well 6 | InGaAs | 3.3 nm | Si: $2 \times 10^{17}/cm^3$ |
| Barrier layer 7 | InAlAs | 1.9 nm | Si: $2 \times 10^{17}/cm^3$ |
| Quantum well 7 | InGaAs | 2.7 nm | Si: $2 \times 10^{17}/cm^3$ |
| Barrier layer 8 | InAlAs | 2.2 nm | Undoped |
| Quantum well 8 | InGaAs | 2.8 nm | Undoped |
| Barrier layer 9 | InAlAs | 1.9 nm | Undoped |
| Quantum well 9 | InGaAs | 2.5 nm | Undoped |

In the QCL 20, the width of the lower contact layer 14b in the Y-axis direction is equal to the width of the substrate 2 in the Y-axis direction, and the width of each of the lower clad layer 13b, the lower guide layer 12b, the active layer 11, the upper guide layer 12a, the upper clad layer 13a, and the upper contact layer 14a in the Y-axis direction is smaller than the width of the substrate 2 in the Y-axis direction. Accordingly, both edge portions of the lower contact layer 14b in the Y-axis direction protrude to both sides in the Y-axis direction from both side surfaces of each of the lower clad layer 13b, the lower guide layer 12b, the active layer 11, the upper guide layer 12a, the upper clad layer 13a, and the upper contact layer 14a in the Y-axis direction.

An insulating film 21 made of, for example, SiN, is formed on each of both side surfaces of the lower clad layer 13b, the lower guide layer 12b, the active layer 11, the upper guide layer 12a, the upper clad layer 13a, and the upper contact layer 14a in the Y-axis direction. An upper electrode 22 made of, for example, Au is formed on the upper contact layer 14a. A lower electrode 23 made of, for example, Au is formed on each of both edge portions of the lower contact layer 14b in the Y-axis direction.

As illustrated in FIGS. 1 and 2, the first QCD 30 is formed on the surface 2a of the substrate 2. More specifically, the first QCD 30 is formed on the surface 2a of the substrate 2 so as to be positioned on one side of the QCL 20 in the X-axis direction. The first QCD 30 includes a first light incident surface 30a that faces the first light-emitting surface 20a of the QCL 20 in the X-axis direction. The first light incident surface 30a is parallel to the Y-Z plane. The width of the first QCD 30 in the Y-axis direction is, for example, about several tens μm, and the length of the first QCD 30 in the X-axis direction is in the range of, for example, about several hundred μm to several mm. A distance between the first light-emitting surface 20a of the QCL 20 and the first light incident surface 30a of the first QCD 30 is, for example, about several hundred μm.

The first QCD 30 includes the same layer structure 10 as the QCL 20, and the active layer 11 of the first QCD 30 has the same quantum cascade structure as the active layer 11 of the QCL 20. The first QCD 30 includes an insulating film 31, an upper electrode 32, and a lower electrode 33, which correspond to the insulating film 21, the upper electrode 22, and the lower electrode 23 of the QCL 20, instead of the insulating film 21, the upper electrode 22, and the lower electrode 23 of the QCL 20.

The second QCD 40 is formed on the surface 2a of the substrate 2. More specifically, the second QCD 40 is formed on the surface 2a of the substrate 2 so as to be positioned on the other side of the QCL 20 in the X-axis direction. The second QCD 40 includes a second light incident surface 40a that faces the second light-emitting surface 20b of the QCL 20 in the X-axis direction. The second light incident surface 40a is parallel to the Y-Z plane. The width of the second QCD 40 in the Y-axis direction is, for example, about several tens μm, and the length of the second QCD 40 in the X-axis direction is in the range of, for example, about several hundred μm to several mm. A distance between the second light-emitting surface 20b of the QCL 20 and the second light incident surface 40a of the second QCD 40 is, for example, about several hundred μm.

The second QCD 40 includes the same layer structure 10 as the QCL 20, and the active layer 11 of the second QCD 40 has the same quantum cascade structure as the active layer 11 of the QCL 20. The second QCD 40 includes an insulating film 41, an upper electrode 42, and a lower electrode 43, which correspond to the insulating film 21, the upper electrode 22, and the lower electrode 23 of the QCL 20, instead of the insulating film 21, the upper electrode 22, and the lower electrode 23 of the QCL 20.

The shape of the first QCD 30 is the same as the shape of the second QCD 40. A distance between the first light-emitting surface 20a of the QCL 20 and the first light incident surface 30a of the first QCD 30 is equal to the distance between the second light-emitting surface 20b of the QCL 20 and the second light incident surface 40a of the second QCD 40. The width of each of the first QCD 30 and the second QCD 40 in the Y-axis direction (a direction parallel to the surface 2a of the substrate 2 and perpendicular to the predetermined direction) is larger than the width of the QCL 20 in the Y-axis direction. Meanwhile, as long as the same characteristics are obtained, the shape of the first QCD 30 does not need to be the same as the shape of the second QCD 40.

The resin member 3 is disposed on all of a second area R2 between the second light-emitting surface 20b of the QCL 20 and the second light incident surface 40a of the second QCD 40, and covers the second light-emitting surface 20b and the second light incident surface 40a. The resin member 3 has optical transparency for the oscillation wavelength of the QCL 20 and an electrical insulation property. The resin member 3 allows the first light-emitting surface 20a of the QCL 20, the first light incident surface 30a of the first QCD 30, and all of a first area R1 between the first light-emitting surface 20a and the first light incident surface 30a to be exposed to the outside. In the fluid analyzer 1A, all of the first area R1 is a first space S1 in which a fluid to be analyzed is disposed.

The fluid analyzer 1A, which is adapted as described above, is used in the following manner in a state in which the fluid analyzer 1A is mounted on, for example, a wiring board. That is, the fluid analyzer 1A is exposed to the atmosphere of a gas to be analyzed, so that the gas to be analyzed is disposed in the first space S1. A bias voltage is applied to the QCL 20 in this state through the upper and lower electrodes 22 and 23, so that laser oscillation occurs in the QCL 20. Accordingly, a laser beam L1 emitted from the first light-emitting surface 20a of the QCL 20 is incident on the first light incident surface 30a of the first QCD 30 through the gas to be analyzed, and a signal is output from the first QCD 30 through the upper and lower electrodes 32 and 33. Further, a laser beam L2 emitted from the second light-emitting surface 20b of the QCL 20 is incident on the second light incident surface 40a of the second QCD 40 through the resin member 3, and a signal is output from the second QCD 40 through the upper and lower electrodes 42 and 43. A processing circuit, which is provided on a subsequent stage, takes a difference between the signal output from the first QCD 30 and the signal output from the second QCD 40, in order to analyze the gas to be analyzed. The signals output from the first QCD 30 and the second QCD 40 are simultaneously acquired in this way, and differential optical absorption spectroscopy measurement is performed in real time for the gas disposed in the first space S1 while the resin member 3 itself is used as a reference material (reference).

Here, the QCL 20 is stably operated in the fluid analyzer 1A for the following reason. That is, the lower electrode 23 is formed in the QCL 20 on each of both the edge portions of the lower contact layer 14b in the Y-axis direction. For this reason, the substrate 2 is made of a semi-insulating semiconductor material, but a current uniformly spreads in the QCL 20 through the lower contact layer 14b when a bias voltage is applied to the QCL 20 through the upper and lower electrodes 22 and 23. Accordingly, the reduction of contact resistance is achieved.

Figure 4:
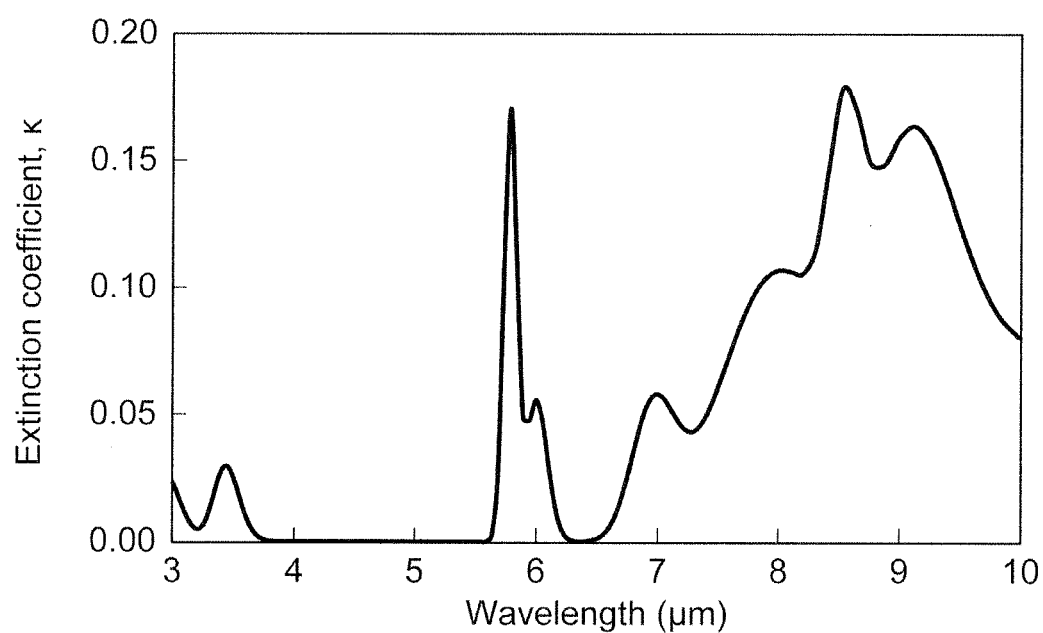
FIG. 4 is a diagram illustrating the absorption coefficient (extinction coefficient) of PAK-01 measured by a spectroscopic ellipsometer.

Meanwhile, "photo-curable resin PAK-01" manufactured by, for example, Toyo Gosei Co., Ltd. can be used as the material of the resin member 3. FIG. 4 is a diagram illustrating the absorption coefficient (extinction coefficient) of PAK-01 measured by a spectroscopic ellipsometer. As illustrated in FIG. 4, PAK-01 is transparent with respect to a wavelength in the range of 3.8 to 5.5 μm and the range of 6.3 to 6.5 μm. When the quantum cascade structure of the active layer 11 is designed so that the oscillation wavelength of the QCL 20 is in the range of 3.8 to 5.5 μm or the range of 6.3 to 6.5 μm in a case in which PAK-01 is used as the material of the resin member 3 (an example shown in Table 1 is an example in which the quantum cascade structure of the active layer 11 is designed so that the oscillation wavelength of the QCL 20 is 6.4 μm), the absorption of the laser beam L2, which is emitted from the second light-emitting surface 20b of the QCL 20, in the resin member 3 can be suppressed. PAK-01 is suitable to detect the absorption of carbon dioxide (a wavelength of 4.3 μm), the absorption of dinitrogen monoxide (a wavelength of 4.5 μm), the absorption of carbon contained in bioorganic molecules caused by the stretching vibration of double bond (amide II band, a wavelength of 6.4 μm), and the like.

Since signals output from the first QCD 30 and the second QCD 40 are simultaneously acquired as described above, the fluid analyzer 1A can perform differential optical absorption spectroscopy measurement for a fluid to be analyzed and can analyze the fluid. Here, in the fluid analyzer 1A, the QCL 20, the first QCD 30, and the second QCD 40 include the same layer structure 10. Accordingly, since the QCL 20, the first QCD 30, and the second QCD 40 have the same quantum cascade structure, the oscillation wavelength of the QCL 20 reliably overlaps the detection wavelength of each of the first QCD 30 and the second QCD 40. Further, in the fluid analyzer 1A, the QCL 20, the first QCD 30, and the second QCD 40 are formed on the surface 2a of the same substrate 2. Accordingly, since the temperatures of the QCL 20, the first QCD 30, and the second QCD 40 are uniformized through the substrate 2, it is difficult for the change in the ambient temperature to affect the result of the differential optical absorption spectroscopy measurement. Therefore, according to the fluid analyzer 1A, a fluid can be accurately analyzed by a simple structure.

Generally, in a quantum cascade laser and a quantum cascade detector including the same layer structure, the detection wavelength region of the quantum cascade detector is wider than the oscillation wavelength region of the quantum cascade laser. However, the detection wavelength region of the quantum cascade detector is much narrower than that of a photodiode or the like and is peaky. Accordingly, when a quantum cascade detector is used as a light-receiving element, it is difficult for the matching between the oscillation wavelength region of the light-emitting element and the detection wavelength region of the quantum cascade detector to be performed. In contrast, in the fluid analyzer 1A, the QCL 20, the first QCD 30, and the second QCD 40 include the same layer structure 10 and are monolithically formed on the same substrate 2. For this reason, even though the matching between the oscillation wavelength region of the QCL 20 and the detection wavelength regions of the first QCD 30 and the second QCD 40 is not particularly performed, the oscillation wavelength region of the QCL 20 reliably overlaps the detection wavelength regions of the first QCD 30 and the second QCD 40. Further, since the detection wavelength region of each of the first QCD 30 and the second. QCD 40 is much narrower than that of a photodiode or the like and each of the first QCD 30 and the second QCD 40 does not have sensitivity with respect to light, which is incident in the Z-axis direction, from a selection side with respect to transition between subbands, the detection of noise light, which is performed by each of the first QCD 30 and the second QCD 40, can be suppressed. Meanwhile, an example in which a quantum cascade laser and a quantum cascade detector are monolithically formed on the same substrate is disclosed in, for example, [Benedikt Schwarz, Peter Reininger, Daniela Ristanic, Hermann Detz, Aaron Maxwell Andrews, Werner Schrenk and Gottfried Strasser, "Monolithically integrated mid-infrared lab-on-a-chip using plasmonics and quantum cascade structures", Nature Communications, Published: 6/Jun./2014, Vol. 5 4085 (2014)].

Furthermore, in the fluid analyzer 1A, the resin member 3 is disposed on all of the second area R2 between the second light-emitting surface 20b of the QCL 20 and the second light incident surface 40a of the second QCD 40 and allows the first light-emitting surface 20a of the QCL 20, the first light incident surface 30a of the first QCD 30, and all of the first area R1 between the first light-emitting surface 20a and the first light incident surface 30a to be exposed to the outside. Accordingly, differential optical absorption spectroscopy measurement can be performed for the fluid (for example, gas) disposed in the first space S1 while the resin member 3 itself is used as a reference material.

Moreover, in the fluid analyzer 1A, the width of each of the first QCD 30 and the second QCD 40 in the Y-axis direction is larger than the width of the QCL 20 in the Y-axis direction. Accordingly, the laser beam L1, which is emitted from the first light-emitting surface 20a of the QCL 20 so as to spread, can be made to be efficiently incident on the first light incident surface 30a of the first QCD 30. Likewise, the laser beam L2, which is emitted from the second light-emitting surface 20b of the QCL 20 so as to spread, can be made to be efficiently incident on the second light incident surface 40a of the second QCD 40.

Figure 5A:
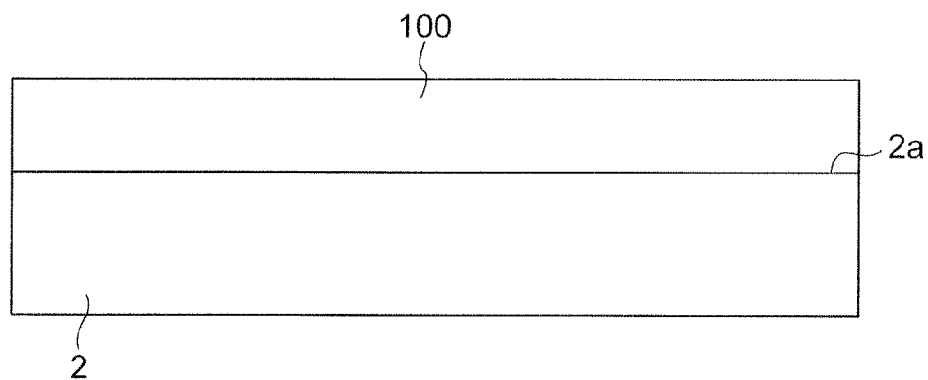
FIGS. 5A and 5B are side views illustrating a method of manufacturing the fluid analyzer of FIG. 1.

Next, a method of manufacturing the fluid analyzer 1A will be described. First, as illustrated in FIG. 5A, a laminated body 100 having a quantum cascade structure is formed on the surface 2a of the substrate 2 (first step). The lower contact layer 14b, the lower clad layer 13b, the lower guide layer 12b, the active layer 11, the upper guide layer 12a, the upper clad layer 13a, and the upper contact layer 14a (see FIG. 3) are sequentially epitaxially grown by molecular beam epitaxy, organometallic vapor-phase epitaxy, or the like, so that the laminated body 100 is obtained.

Figure 5B:
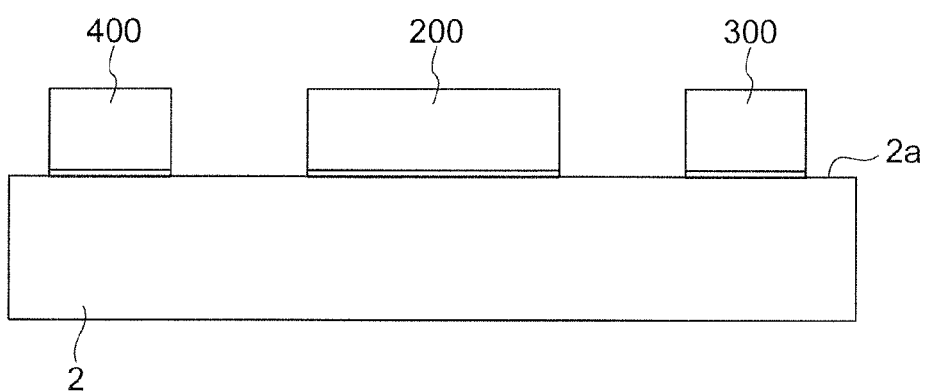
Figure 6A:
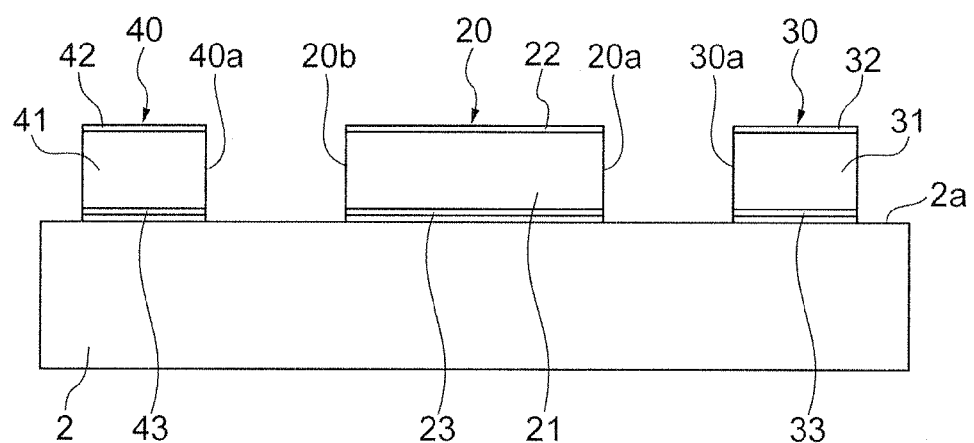
FIGS. 6A and 6B are side views illustrating the method of manufacturing the fluid analyzer of FIG. 1.

Subsequently, etching is performed on the laminated body 100 as illustrated in FIG. 5B, and thereby a portion 200 corresponding to the layer structure 10 of the QCL 20, a portion 300 corresponding to the layer structure 10 of the first QCD 30, and a portion 400 corresponding to the layer structure 10 of the second QCD 40 are formed (second step). A photolithographic technique and an etching technique can be used to form the respective portions 200, 300, and 400. However, a dry etching technique, such as ICP, may be used to obtain the first light-emitting surface 20a, the second light-emitting surface 20b, the first light incident surface 30a, and the second light incident surface 40a that are excellent in perpendicularity to the surface 2a of the substrate 2. Meanwhile, areas, which are present between the respective portions 200, 300, and 400, of the lower contact layer 14b are removed, so that the respective portions 200, 300, and 400 are electrically isolated from each other. Subsequently, as illustrated in FIG. 6A, the upper and lower electrodes 22 and 23 are formed on the portion 200 with the insulating film 21 interposed between the upper and lower electrodes 22 and 23, the upper and lower electrodes 32 and 33 are formed on the portion 300 with the insulating film 31 interposed between the upper and lower electrodes 32 and 33, and the upper and lower electrodes 42 and 43 are formed on the portion 400 with the insulating film 41 interposed between the upper and lower electrodes 42 and 43, so that the QCL 20, the first QCD 30, and the second QCD 40 are obtained (second step).

Figure 6B:
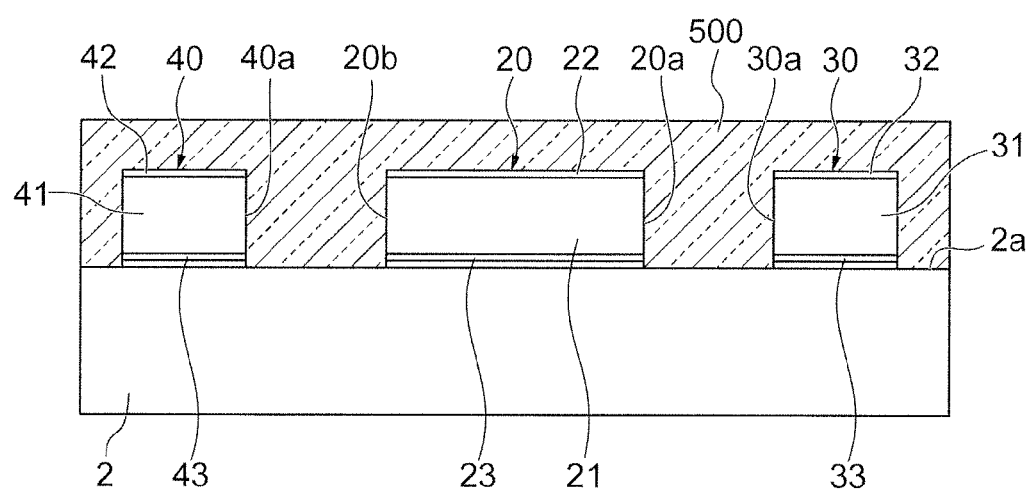
Figure 7A:
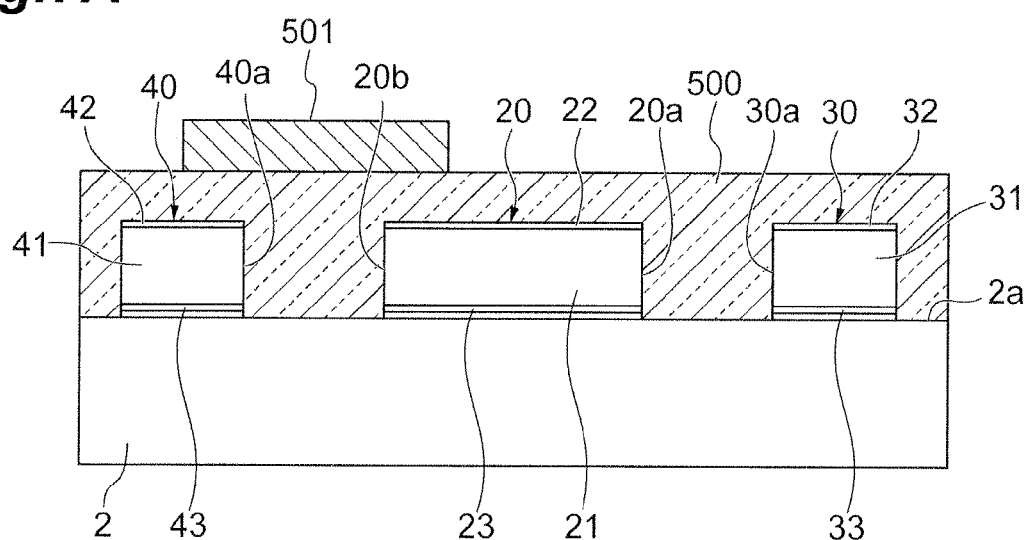
FIGS. 7A and 7B are side views illustrating the method of manufacturing the fluid analyzer of FIG. 1.
Figure 7B:
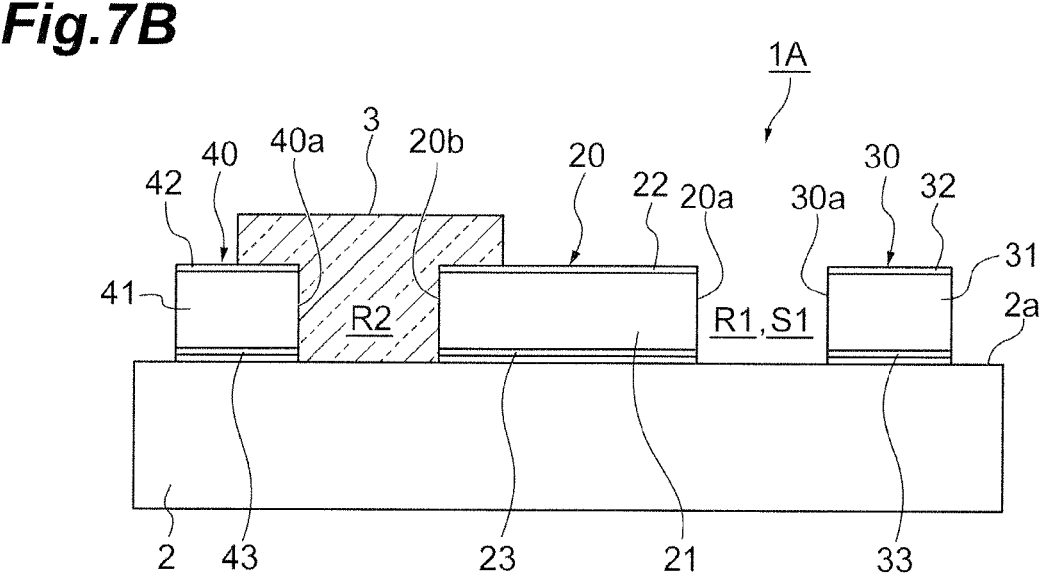

Subsequently, as illustrated in FIG. 6B, a resin layer 500, which has optical transparency for the oscillation wavelength of the QCL 20 and an electrical insulation property, is formed on the surface 2a of the substrate 2 so as to cover the QCL 20, the first QCD 30, and the second QCD 40 (third step). An ultraviolet curable resin material is applied to the surface 2a of the substrate 2 by, for example, spin coating and is then cured by the irradiation of ultraviolet light, so that the resin layer 500 is obtained. Subsequently, etching is performed on the resin layer 500 as illustrated in FIGS. 7A and 7B, and the resin member 3 is formed and the first space S1 is formed in the first area R1 between the first light-emitting surface 20a of the QCL 20 and the first light incident surface 30a of the first QCD 30 (fourth step). More specifically, a photoresist 501 is patterned on the resin layer 500 as illustrated in FIG. 7A and reactive ion etching is performed on the resin layer 500 as illustrated in FIG. 7B to form the resin member 3 and to form the first space S1 in the first area R1.

The above-mentioned respective steps are sequentially performed to obtain the fluid analyzer 1A. Meanwhile, the above-mentioned respective steps are sequentially performed at a wafer level and a wafer is diced at the last, so that a plurality of fluid analyzers 1A can be obtained. In this case, an end face of the wafer facing the first light incident surface 30a of the first QCD 30 and an end face of the wafer facing the second light incident surface 40a of the second QCD 40 may be cut surfaces, such as cleavage surfaces, at the time of dicing.

According to the method of manufacturing the fluid analyzer 1A, the fluid analyzer 1A can be easily and reliably manufactured as described above. Particularly, the QCL 20, the first QCD 30, and the second QCD 40 having the same quantum cascade structure can be formed on the surface 2a of the substrate 2 with a high positional accuracy.

Second Embodiment

Figure 8:
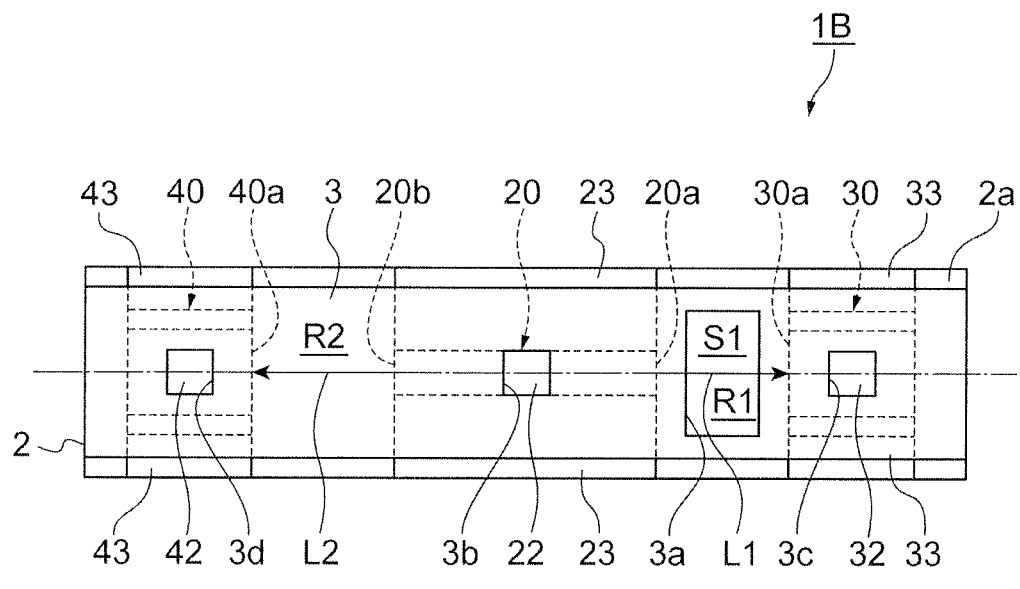
FIG. 8 is a plan view of a fluid analyzer according to a second embodiment of the disclosure.
Figure 9:
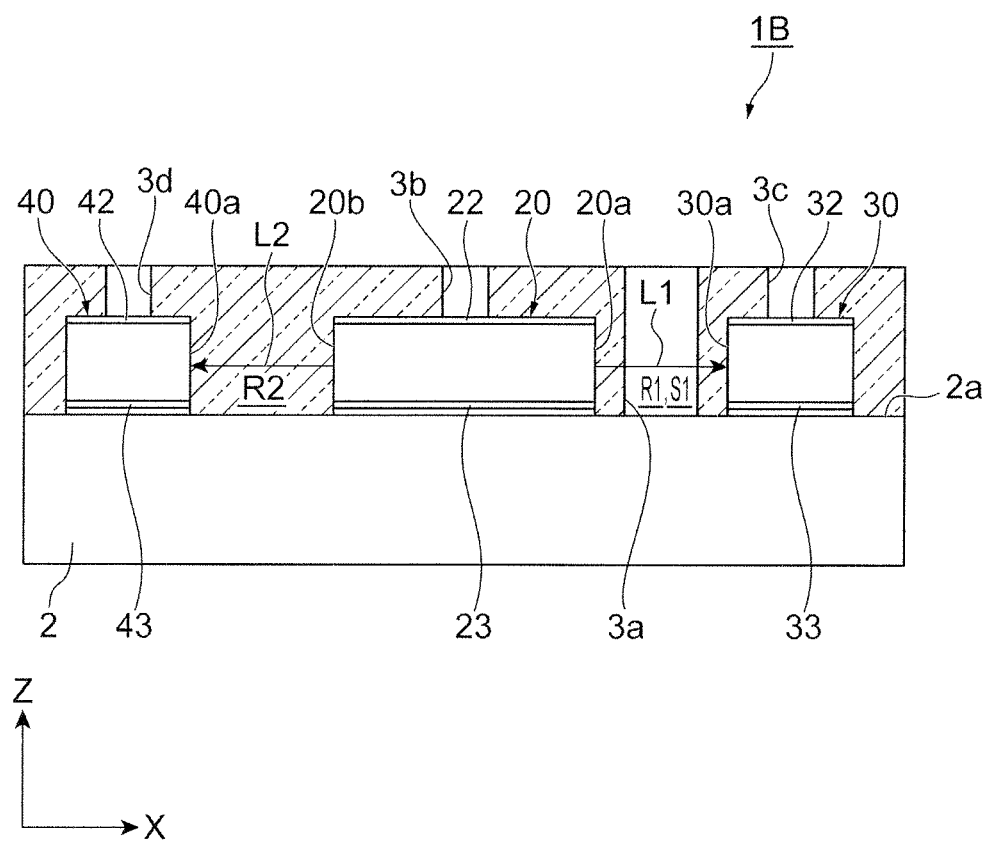
FIG. 9 is a side view of the fluid analyzer of FIG. 8.

As illustrated in FIGS. 8 and 9, a fluid analyzer 1B is mainly different from the above-mentioned fluid analyzer 1A in terms of the structure of a resin member 3. Meanwhile, only the resin member 3 is illustrated in FIG. 9 as a section taken along a dashed-dotted line of FIG. 8.

In the fluid analyzer 1B, the resin member 3 includes a first recess 3a defining a first space S1 in a first area R1 between a first light-emitting surface 20a of a QCL 20 and a first light incident surface 30a of a first QCD 30 and covers the first light-emitting surface 20a and the first light incident surface 30a. The first recess 3a is opened to the side opposite to a substrate 2, and the bottom of the first recess 3a is a surface 2a of the substrate 2. The resin member 3 is the same as the resin member 3 of the above-mentioned fluid analyzer 1A in that the resin member 3 is disposed on all of the second area R2 between a second light-emitting surface 20b of the QCL 20 and a second light incident surface 40a of a second QCD 40.

The resin member 3 further includes a recess 3b that allows an upper electrode 22 of the QCL 20 to be exposed to the outside, a recess 3c that allows an upper electrode 32 of the first QCD 30 to be exposed to the outside, and a recess 3d that allows an upper electrode 42 of the second QCD 40 to be exposed to the outside. The respective upper electrodes 22, 32, and 42 can come into electrical contact with external wiring through the corresponding respective recesses 3b, 3c, and 3d. Since outer edge portions of lower electrodes 23, 33, and 43 are not covered with the resin member 3, the lower electrodes 23, 33, and 43 can come into electrical contact with external wiring through the outer edge portions thereof. Meanwhile, when a fluid to be analyzed is liquid, the respective recesses 3b, 3c, and 3d and the respective lower electrodes 23, 33, and 43 may be covered with the resin member (that is, each of the QCL 20, the first QCD 30, and the second QCD 40 may be covered with the resin member as a whole) to prevent the adhesion of the fluid and the like after the respective upper electrodes 22, 32, and 42 come into electrical contact with the external wiring and the respective lower electrodes 23, 33, and 43 come into electrical contact with the external wiring.

According to the fluid analyzer 1B, a fluid can be accurately analyzed by a simple structure as described above as in the above-mentioned fluid analyzer 1A.

Further, in the fluid analyzer 1B, the resin member 3 is disposed on all of the second area R2, includes the first recess 3*a* defining the first space S1 in the first area R1, and covers the first light-emitting surface 20*a* of the QCL 20 and the first light incident surface 30*a* of the first QCD 30. Accordingly, differential optical absorption spectroscopy measurement can be performed for the fluid (for example, gas or liquid) disposed in the first space S1 while the resin member 3 itself is used as a reference material.

Particularly, in the fluid analyzer 1B, the first space S1 is defined by the first recess 3*a* of the resin member 3 and the first recess 3*a* is opened to the side opposite to the substrate 2. Accordingly, when the fluid to be analyzed is liquid, the liquid can be stably disposed in the first space S1 by a micropipette or the like. Furthermore, since the first light-emitting surface 20*a* of the QCL 20 and the first light incident surface 30*a* of the first QCD 30 are covered with the resin member 3 even when the liquid, which is the fluid to be analyzed, is disposed in the first space S1, an electrical insulation property can be ensured. Moreover, since a small amount of sample can be analyzed, a burden on a subject can be reduced when, for example, saliva, blood, sweat, urine, and the like are analyzed.

Third Embodiment

Figure 10:
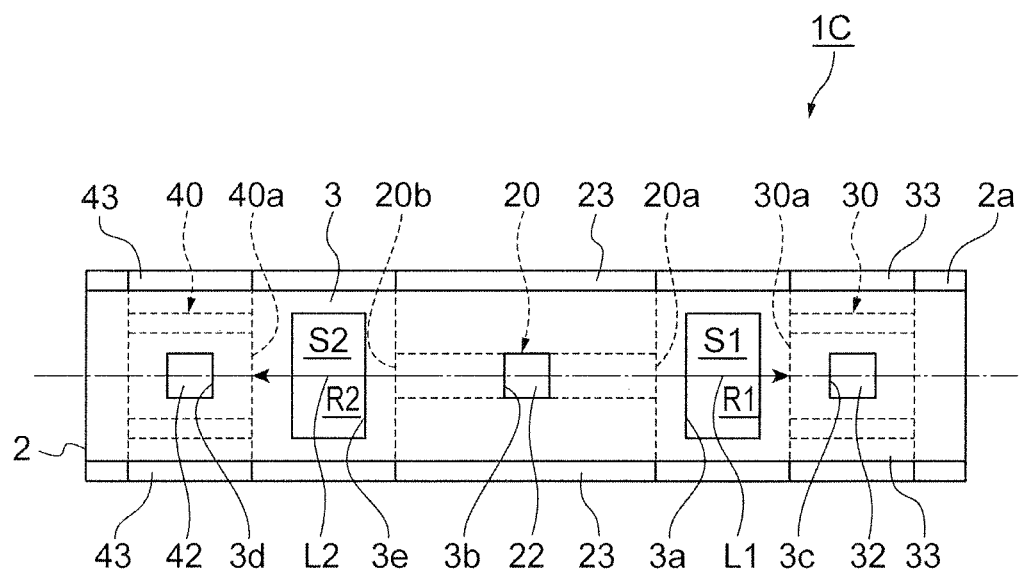
FIG. 10 is a plan view of a fluid analyzer according to a third embodiment of the disclosure.
Figure 11:
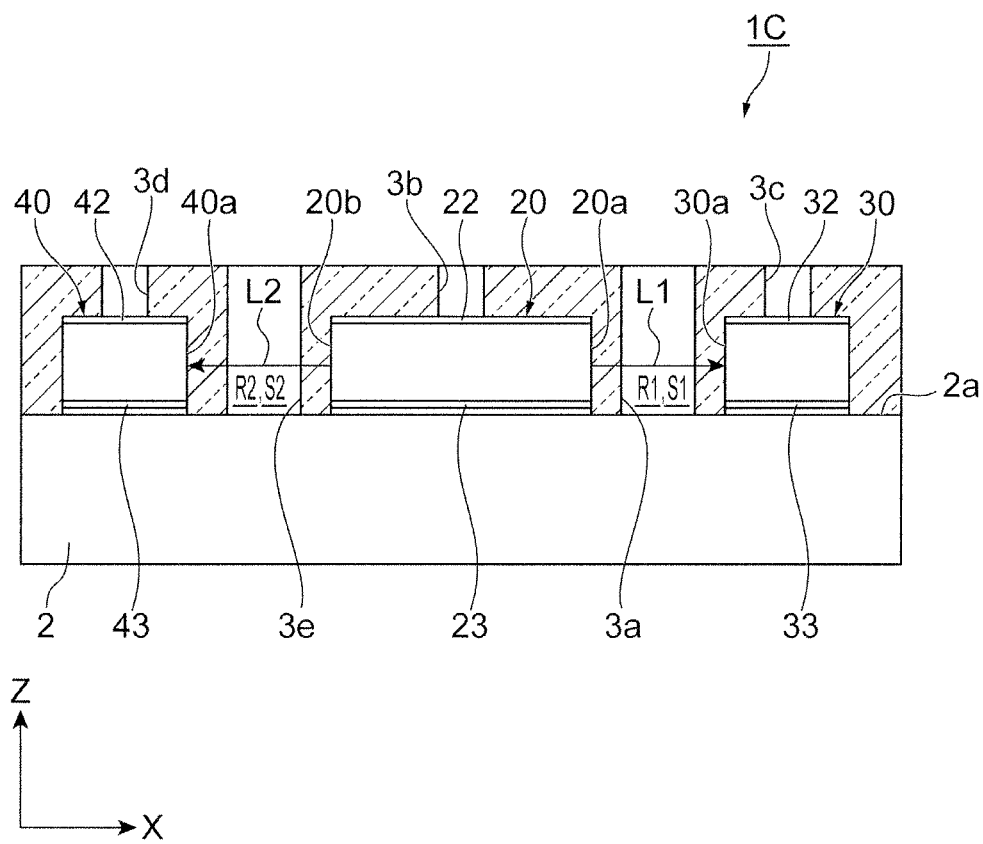
FIG. 11 is a side view of the fluid analyzer of FIG. 10.

As illustrated in FIGS. 10 and 11, a fluid analyzer 1C is mainly different from the above-mentioned fluid analyzer 1A in terms of the structure of a resin member 3. Meanwhile, only the resin member 3 is illustrated in FIG. 11 as a section taken along a dashed-dotted line of FIG. 10.

In the fluid analyzer 1C, the resin member 3 includes a first recess 3*a* defining a first space S1 in a first area R1 between a first light-emitting surface 20*a* of a QCL 20 and a first light incident surface 30*a* of a first QCD 30 and covers the first light-emitting surface 20*a* and the first light incident surface 30*a*. The first recess 3*a* is opened to the side opposite to a substrate 2, and the bottom of the first recess 3*a* is a surface 2*a* of the substrate 2. Further, the resin member 3 includes a second recess 3*e* defining a second space S2 in a second area R2 between a second light-emitting surface 20*b* of the QCL 20 and a second light incident surface 40*a* of a second QCD 40 and covers the second light-emitting surface 20*b* and the second light incident surface 40*a*. The second recess 3*e* is opened to the side opposite to the substrate 2, and the bottom of the second recess 3*e* is the surface 2*a* of the substrate 2.

The resin member 3 further includes a recess 3*b* that allows an upper electrode 22 of the QCL 20 to be exposed to the outside, a recess 3*c* that allows an upper electrode 32 of the first QCD 30 to be exposed to the outside, and a recess 3*d* that allows an upper electrode 42 of the second QCD 40 to be exposed to the outside. The respective upper electrodes 22, 32, and 42 can come into electrical contact with external wiring through the corresponding respective recesses 3*b*, 3*c*, and 3*d*. Since outer edge portions of lower electrodes 23, 33, and 43 are not covered with the resin member 3, the lower electrodes 23, 33, and 43 can come into electrical contact with external wiring through the outer edge portions thereof. Meanwhile, when a fluid to be analyzed is liquid, the respective recesses 3*b*, 3*c*, and 3*d* and the respective lower electrodes 23, 33, and 43 may be covered with the resin member (that is, each of the QCL 20, the first QCD 30, and the second QCD 40 may be covered with the resin member as a whole) to prevent the adhesion of the fluid and the like after the respective upper electrodes 22, 32, and 42 come into electrical contact with the external wiring and the respective lower electrodes 23, 33, and 43 come into electrical contact with the external wiring.

According to the fluid analyzer 1C, a fluid can be accurately analyzed by a simple structure as described above as in the above-mentioned fluid analyzer 1A.

Further, in the fluid analyzer 1C, the resin member 3 includes the first recess 3*a* defining the first space S1 in the first area R1 and covers the first light-emitting surface 20*a* of the QCL 20 and the first light incident surface 30*a* of the first QCD 30. Furthermore, the resin member 3 includes the second recess 3*e* defining the second space S2 in the second area R2 and covers the second light-emitting surface 20*b* of the QCL 20 and the second light incident surface 40*a* of the second QCD 40. Accordingly, while a predetermined material is disposed in the second space S2 and the material is used as a reference material, differential optical absorption spectroscopy measurement can be performed for the fluid (for example, gas or liquid) disposed in the first space S1.

For example, when a solution, which include a predetermined solvent and a predetermined solute, is disposed in the first recess 3*a* defining the first space S1 and a solution, which includes only the predetermined solvent, (that is, a solution from which the predetermined solute has been removed) is disposed in the second recess 3*e* defining the second space S2, absorption characteristics of only the predetermined solute excluding an influence of the predetermined solvent can be evaluated.

Particularly, in the fluid analyzer 1C, the first space S1 is defined by the first recess 3*a* of the resin member 3 and the first recess 3*a* is opened to the side opposite to the substrate 2. Accordingly, when the fluid to be analyzed is liquid, the liquid can be stably disposed in the first space S1 by a micropipette or the like. Likewise, the second space S2 is defined by the second recess 3*e* of the resin member 3 and the second recess 3*e* is opened to the side opposite to the substrate 2. Accordingly, when the predetermined material serving as the reference material is liquid, the liquid can be stably disposed in the second space S2 by a micropipette or the like. Further, since the first light-emitting surface 20*a* of the QCL 20 and the first light incident surface 30*a* of the first QCD 30 are covered with the resin member 3 even when the liquid, which is the fluid to be analyzed, is disposed in the first space S1, an electrical insulation property can be ensured. Likewise, since the second light-emitting surface 20*h* of the QCL 20 and the second light incident surface 40*a* of the second QCD 40 are covered with the resin member 3 even when the liquid, which is the predetermined material as the reference material, is disposed in the second space S2, an electrical insulation property can be ensured. Furthermore, since a small amount of sample can be analyzed, a burden on a subject can be reduced when, for example, saliva, blood, sweat, urine, and the like are analyzed.

The first embodiment, the second embodiment, and the third embodiment of this disclosure have been described above, but one aspect of the disclosure is not limited to each of the above-mentioned embodiments. For example, the layer structure 10 of each of the QCL 20, the first QCD 30, and the second QCD 40 is not limited to the above-mentioned layer structure. Further, the quantum cascade structure of the active layer 11 of the layer structure 10 is also not limited to the above-mentioned quantum cascade structure.

For example, in each of the above-mentioned embodiments, a diffraction grating layer may be provided in the layer structure 10 so that the QCL 20 is formed as a distributed feedback (DFB) element. According to this structure, single-mode oscillation can be obtained in the QCL 20 and more accurate spectroscopic measurement can be performed.

Figure 12A:
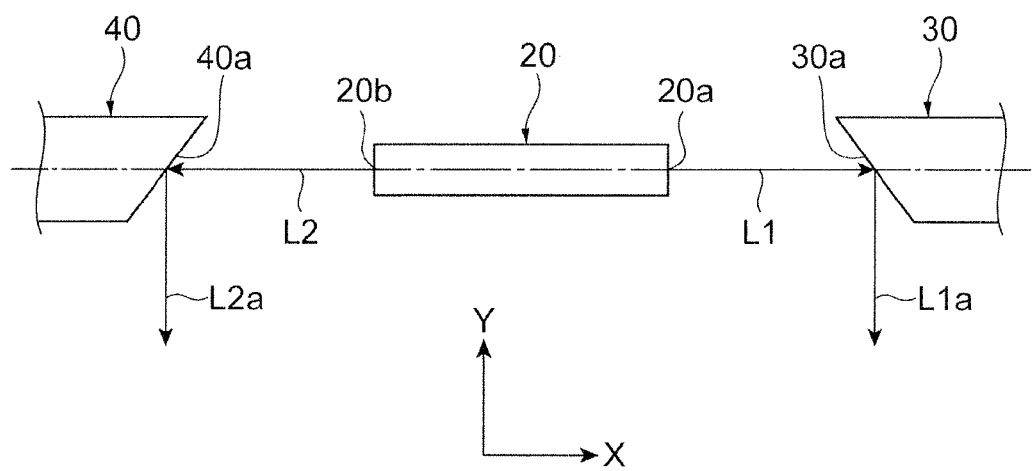
FIGS. 12A and 12B are plan views of a part of a fluid analyzer according to a modification.
Figure 12B:
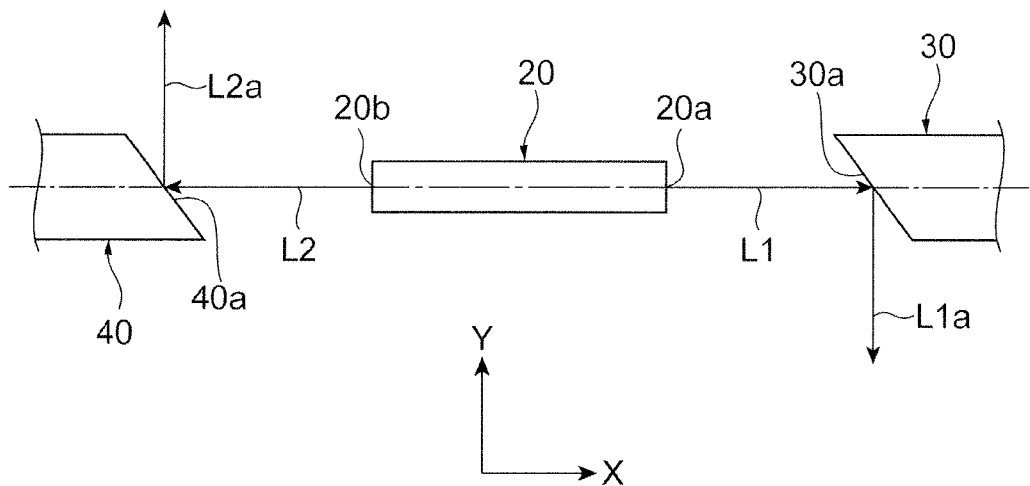

In this case, the first light incident surface 30a of the first QCD 30 may be inclined so as to have a positional relationship where an acute angle is formed between the first light incident surface 30a of the first QCD 30 and the first light-emitting surface 20a of the QCL 20 as illustrated in. FIGS. 12A and 12B. Likewise, the second light incident surface 40a of the second QCD 40 may be inclined so as to have a positional relationship where an acute angle is formed between the second light incident surface 40a of the second QCD 40 and the second light-emitting surface 20b of the QCL 20. Accordingly, since light L1a, which is reflected by the first light incident surface 30a of the first QCD 30, of the laser beam L1 becomes return light, it is suppressed that the light L1a is incident on the first light-emitting surface 20a of the QCL 20. Since light L2a, which is reflected by the second light incident surface 40a of the second QCD 40, of the laser beam L2 becomes return light, it is suppressed that the light L2a is incident on the second light-emitting surface 20b of the QCL 20. Accordingly, since it is suppressed that the oscillation mode caused by DFB is disturbed due to an influence of the return light, stable single-mode oscillation can be obtained in the QCL 20.

In the examples illustrated in FIGS. 12A and 12B, each of the first light incident surface 30a of the first QCD 30 and the second light incident surface 40a of the second QCD 40 is inclined so as to form a right angle with an X-Y plane perpendicular to the Z-axis direction and so as to form an angle of 45° with the Y-Z plane perpendicular to the X-axis direction. The first QCD 30 including the inclined first light incident surface 30a and the second QCD 40 including the inclined second light incident surface 40a can be formed by etching that is performed on the laminated body 100 by a photolithographic technique.

As described above, each of a distance between the first light-emitting surface 20a of the QCL 20 and the first light incident surface 30a of the first QCD 30 and a distance between the second light-emitting surface 20b of the QCL 20 and the second light incident surface 40a of the second QCD 40 is, for example, about several hundred μm. For this reason, it is very difficult to form an antireflection coating, which is formed of, for example, a dielectric multilayer, on each of the first light incident surface 30a of the first QCD 30 and the second light incident surface 40a of the second QCD 40. Accordingly, inclining each of the first light incident surface 30a of the first QCD 30 and the second light incident surface 40a of the second QCD 40 is very important to obtain stable single-mode oscillation in the QCL 20 formed as a DFB element.

Meanwhile, each of the first light incident surface 30a of the first QCD 30 and the second light incident surface 40a of the second QCD 40 may be inclined so that the light L1a and the light L2a travel to the same side as illustrated in FIG. 12A. Alternatively, each of the first light incident surface 30a of the first QCD 30 and the second light incident surface 40a of the second QCD 40 may be inclined so that the light L1a and the light L2a travel to sides different from each other as illustrated in FIG. 12B.

What is claimed is:

1. A fluid analyzer comprising:
   a substrate;
   a quantum cascade laser formed on a surface of the substrate and including a first light-emitting surface and a second light-emitting surface facing each other in a predetermined direction parallel to the surface;
   a first quantum cascade detector formed on the surface and including the same layer structure as the quantum cascade laser and a first light incident surface facing the first light-emitting surface in the predetermined direction;
   a second quantum cascade detector formed on the surface and including the same layer structure as the quantum cascade laser and a second light incident surface facing the second light-emitting surface in the predetermined direction; and
   a resin member covering at least the second light-emitting surface and the second light incident surface and having optical transparency for an oscillation wavelength of the quantum cascade laser, and an electrical insulation property,
   wherein a first space in which a fluid to be analyzed is disposed is provided in a first area between the first light-emitting surface and the first light incident surface.

2. The fluid analyzer according to claim 1,
   wherein the resin member is disposed on all of a second area between the second light-emitting surface and the second light incident surface, and allows the first light-emitting surface, the first light incident surface, and all of the first area to be exposed to the outside.

3. The fluid analyzer according to claim 1,
   wherein the resin member is disposed on all of a second area between the second light-emitting surface and the second light incident surface, and includes a first recess defining the first space in the first area and covers the first light-emitting surface and the first light incident surface.

4. The fluid analyzer according to claim 3,
   wherein the first recess is opened to a side opposite to the substrate.

5. The fluid analyzer according to claim 1,
   wherein the resin member includes a second recess defining a second space in a second area between the second light-emitting surface and the second light incident surface and covers the second light-emitting surface and the second light incident surface, and includes a first recess defining the first space in the first area and covers the first light-emitting surface and the first light incident surface.

6. The fluid analyzer according to claim 5,
   wherein each of the first recess and the second recess is opened to a side opposite to the substrate.

7. The fluid analyzer according to claim 1,
   wherein the width of each of the first quantum cascade detector and the second quantum cascade detector in a direction parallel to the surface and perpendicular to the predetermined direction is larger than the width of the quantum cascade laser in the direction parallel to the surface and perpendicular to the predetermined direction.

8. The fluid analyzer according to claim 1,
   wherein the quantum cascade laser is formed as a distributed feedback element,
   the first light incident surface is inclined so as to have a positional relationship where an acute angle is formed between the first light incident surface and the first light-emitting surface, and the second light incident surface is inclined so as to have a positional relationship where an acute angle is formed between the second light incident surface and the second light-emitting surface.

9. A method of manufacturing a fluid analyzer, the method comprising:
- a first step of forming a laminated body on a surface of a substrate, the laminated body including a quantum cascade structure;
- a second step of performing etching on the laminated body, and forming a quantum cascade laser including a first light-emitting surface and a second light-emitting surface facing each other in a predetermined direction parallel to the surface, a first quantum cascade detector including a first light incident surface facing the first light-emitting surface in the predetermined direction, and a second quantum cascade detector including a second light incident surface facing the second light-emitting surface in the predetermined direction;
- a third step of forming a resin layer on the surface, the resin layer having optical transparency for an oscillation wavelength of the quantum cascade laser and an electrical insulation property, so that the resin layer covers the quantum cascade laser, the first quantum cascade detector, and the second quantum cascade detector; and
- a fourth step of performing etching on the resin layer, and forming a resin member covering at least the second light-emitting surface and the second light incident surface and forming a first space, in which a fluid to be analyzed is disposed, in a first area between the first light-emitting surface and the first light incident surface.

* * * * *